United States Patent [19]

Milnes et al.

[11] Patent Number: 4,650,550

[45] Date of Patent: Mar. 17, 1987

[54] MANUFACTURE AND REPAIR OF DENTAL APPLIANCES

[75] Inventors: Ian M. Milnes, Mechanicsburg; Louis H. Tateosian, York, both of Pa.

[73] Assignee: Dentsply Research and Development Corporation, York, Pa.

[21] Appl. No.: 710,522

[22] Filed: Mar. 12, 1985

Related U.S. Application Data

[63] Continuation of Ser. No. 370,215, Apr. 20, 1982, abandoned.

[51] Int. Cl.[4] .................................................. A61C 5/08
[52] U.S. Cl. .................................. 204/38.7; 204/37.1; 433/202.1; 427/2; 427/409
[58] Field of Search ............... 204/38.1, 38.7, 37.1; 427/2, 409; 433/199, 200, 201, 202, 203, 206, 207, 208, 217, 222; 264/19, 20

[56] References Cited

U.S. PATENT DOCUMENTS

| | | | |
|---|---|---|---|
| 2,558,139 | 8/1947 | Knock et al. | 260/45.5 |
| 2,916,469 | 12/1959 | Lal | 433/228 X |
| 3,889,385 | 6/1975 | Dougherty | 32/12 |
| 3,997,637 | 12/1976 | Rogers | 264/19 |
| 4,064,311 | 12/1977 | McLean et al. | 428/434 |
| 4,125,442 | 11/1978 | Rogers | 204/38 C |
| 4,247,575 | 1/1981 | O'Connell et al. | 427/2 |
| 4,295,941 | 10/1981 | Lustgarten | 204/35 R |
| 4,364,731 | 12/1982 | Norling et al. | 433/218 |
| 4,427,501 | 1/1984 | Rogers | 204/37.1 |
| 4,478,579 | 10/1984 | Fischer et al. | 433/222 |

FOREIGN PATENT DOCUMENTS

| | | | |
|---|---|---|---|
| 490138 | 11/1976 | Australia | 433/222 |
| 0047097 | 3/1982 | European Pat. Off. | |
| 1115544 | 5/1968 | United Kingdom. | |

OTHER PUBLICATIONS

McLean, "Aesthetics in Restorative Dentistry: The Challenge for the Future", 1980, vol. 149, p. 368, et. seq.

Primary Examiner—John F. Niebling
Assistant Examiner—William T. Leader
Attorney, Agent, or Firm—Woodcock Washburn Kurtz Mackiewicz & Norris

[57] ABSTRACT

Methods for the manufacture and repair of dental appliance prostheses are provided comprising providing a shaped metallic underlayment, and plating onto at least a portion of the underlayment a layer of a second metallic species. An amount sufficient substantially to obscure the layer, of a polymerizable opaqueing agent is then applied to the layer. Following polymerization of the opaqueing agent through application of heat or radiant energy, especially visible light, the layer is ideally suited for the application of dental aesthetic veneers or other surfacing materials. In accordance with the preferred embodiment, an adhesion promotion species is employed either in a separate treating step for the second metallic layer or through inclusion thereof in the opaqueing agent.

26 Claims, 2 Drawing Figures

MANUFACTURE AND REPAIR OF DENTAL APPLIANCES

This is a continuation of application Ser. No. 370,215, filed Apr. 20, 1982 now abandoned.

BACKGROUND OF THE INVENTION

This invention is directed to methods for the manufacture and repair of dental appliances especially crowns and bridges. More particularly, a system is provided whereby dental appliances may be fabricated or repaired in the mouth or externally. Such methods are provided which provide dental appliances which are physically and aesthetically superior to those presently known. In addition, this invention is directed to materials useful for the preparation of dental appliances and for the repair thereof which have the ability to bond to metallic underlayments or substrates with improved tenacity.

The fracture of porcelain from fixed dental appliances such as crowns and bridge work has been a problem for dentists for many years. The repair of such prostheses has been accomplished in the past in two ways. Typically, a prostheses is removed from the patient's mouth and repaired in a dental laboratory. This procedure may be quite painful and traumatic to the patient. Further, damage to existing dentition and/or to the dental appliance itself is frequently encountered. This procedure requires extensive amounts of practitioner time in the mouth with attendant expense. In the alternative, it has been known to repair dental appliances while they remain fixed within a patient's mouth. While this effects a substantial savings in working time in the mouth, prior methods and materials have provided only mediocre aesthetic results having a relatively short lifetime.

It will be appreciated that the construction and repair of dental appliances necessarily involve the bonding of materials to dental metals. Such prosthetic devices generally comprise shaped metallic underlayments which are fabricated from a metallic species or alloy having good strength, durability, etc. and also compatability with the oral environment. Such alloys, which frequently include high gold alloys, are generally inert and provide a difficult bonding surface. Accordingly, prior art materials and methods which involve the application of polymerizable adhesives and other materials to the surface of dental alloys have had poor bond strengths and concomitant poor durabilities. Efforts to overcome these shortcomings have not been successful. For example, a cold-setting ethoxylated bisphenol-A dimethacrylate resin sold by the Denmat Company incorporates certain silanous materials such as γ-methacryloxypropyltrimethoxysilane and other materials as adhesion promoters for application to dental metals. Such material does not provide permanent bonding to dental alloys, however. Fusion TM is a two component material, (believed to be a silane-based product) which has been sold as an adhesion promoter. Metalit TM is a cyanoacrylate based system which, again, is believed to provide only a temporary bond to dental alloys in the oral environment. It is believed that when applied to dental alloys, the foregoing materials bond only weakly to the metal. It is further believed that oral fluids are capable of hydrolyzing or otherwise destroying this bonding causing a loss of adhesion to the metal underlayment or substrate.

U.S. Pat. No. 3,889,385 issued to Dougherty discloses dental opaqueing materials comprising copolymers of methyl methacrylate and acrylonitrile in a solvent medium. Small amounts of acrylic or methacrylic acid may be included in these compositions as may certain silanes.

U.S. Pat. No. 3,997,637 issued to Rogers discloses methods for making tooth reconstructions employing electrodeposition techniques. U.S. Pat. No. 4,125,442 also to Rogers discloses the preparation of composite tooth reconstructions by bonding porcelain over a basis metal coated with electrolytically deposited metal to improve the bond strength of the porcelain to the metal.

U.S. Pat. No. 4,247,575 issued to O'Connell et al is directed to methods for electroless plating of silver onto tooth structures, especially dentin.

U.S. Pat. No. 4,295,951 to Lustgarten provides improved porcelain coated metal dental articles through electroplating gold over a non-precious metal substrate, adding finely divided gold particles thereto and firing porcelainic materials thereover.

McLean in "Aesthetics and Restorative Dentistry: The Challenge for the Future" British Dent. Journal Vol. 149, pp. 368 et. seq. (1980) suggests the coating of nickel-chrome with noble metals such as gold, platinum or rhodium by electroplating followed by plating to improve the receptivity of the metal to porcelain coatings.

None of the foregoing discloses or suggests the novel methods and materials of the present invention.

SUMMARY OF THE INVENTION

This invention provides methods for the manufacture of dental appliances and prostheses and for their repair. Additionally, materials suitable for use in the practice of such methods are comprehended by the present invention. According to a preferred embodiment, dental appliances are prepared by providing a shaped, metallic underlayment. Onto at least a portion of the metallic underlayment is plated a layer of a second metallic species. An amount sufficient substantially to obscure the layer of the second metallic species of a polymerizable opaqueing agent is then applied to the layer and subsequently polymerized. The opequeing material tightly adheres to the second metallic layer and obscures the same from view. It is preferred that an adhesion promoter be employed in accordance with the present methods. Thus, an adhesion promoter may be applied to the second metallic layer prior to the application of the opaqueing agent. In the alternative, the adhesion promoter may be included as a component of the opaqueing agent. The opaqued portion is well adapted for the application of a cosmetic or aesthetic veneer thereto.

It is preferred that the opaqueing agent be curable or polymerizable through exposure to actinic radiation such as to visible light. It is also preferred that the adhesion promoter, if used, comprise a material having dual chemical functionality. Thus, a first functionality comprises one or more polymerizable groups while the second functionality is selected to be capable of bonding with the surface of the second metallic species either ionically, coordinately, or covalently.

The foregoing methods and materials are suitable for construction of dental articles either within the mouth or externally. Thus, crowns, bridges, temporary bridges, and a wide variety of other oral prosthetics may be so constructed or repaired.

DETAILED DESCRIPTION OF THE INVENTION

Figure 1:
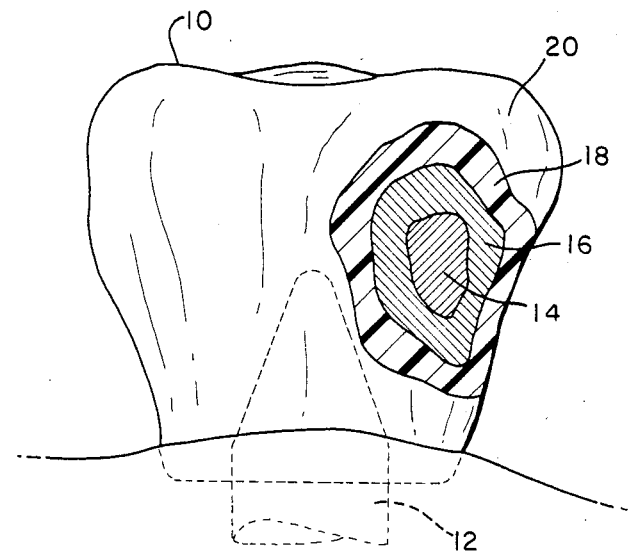
FIG. 1 is a partially cut away view of an artifical dental crown formed in accordance with the present invention. This figure discloses a metallic underlayment, plated second metallic species, and opaqueing agent in addition to an external aesthetic facing veneer.

The present invention is directed to methods for the manufacture and repair of dental appliances and prostheses and to materials useful in such methods. In accordance with the present invention there is provided a shaped, metallic underlayment which will generally comprise a dental alloy material. A layer of a second metallic species is then plated onto at least a portion of the underlayment to provide a surface more hospitable toward bonding with polymerizable species. To the layer is then applied an amount sufficient subtantially to obscure the layer of a polymerizable opaqueing agent which is subsequently polymerized. It is preferred that the layer of a second metallic specie be treated with an adhesion promoter prior to applying the opaqueing agent. In the alternative, it is possible to combine an adhesion promoter together with the opaqueing agent or to apply the two species concurrently.

The foregoing procedures provide a surface of polymerized material on the surface of a shaped metallic underlayment. By virtue of the imposition of a second metallic species arrived at through a plating technique between the metallic underlayment and the polymerized material, superior bonding of the polymerized species to the underlayment takes place. The layer of polymerized material is designed substantially to obscure the layer of second metallic specie so that the aesthetic detraction of an intraoral metallic mass is avoided. The polymerized layer is excellantly well suited for the application of additional species thereto. Accordingly, aesthetic veneers and the like may be applied to this layer to effect the construction of a wide variety of dental appliances such as crowns, bridges, and other devices. Alternatively, additional layers of polymerizable materials may be built up on the surface of the metallic underlayment and either smoothed or sculpted to result in a pleasing appearance for a dental object formed thereby.

The shaped, metallic underlayment which is provided during the course of the practice of the methods of this invention may comprise any of a wide variety of metallic species which are known for use in the preparation of dental appliances and prostheses. Accordingly, metallic forms for crowns, bridges oral structures, artificial teeth, and a wide variety of other intraoral metallic foundation objects or underlayments may be so employed. Those skilled in the art will appreciate that, in general, such underlayments will comprise one of a number of dental alloys or metal materials such as for example, gold, nickel, silver, platinum etc. together with alloys of the foregoing, and a wide variety of other metallic species. In general, such shaped metallic objects will be formulated so as to have little or no physiological effects in the mouth of a patient. Accordingly, such materials are generally considered to be inert and possessed of a relatively passive metal surface.

In accordance with the present invention, at least a portion of the shaped, metallic underlayments are plated with a layer of a second metallic species. The second metallic species is selected to be one which forms stronger bonds with the opaqueing agents of the present invention than do the metallic underlayments. Accordingly, it is desired to provide such second metallic species which are less inert to bonding than are the dental alloys comprising the shaped metallic underlayments. It is preferred that such second metallic species be materials such as tin, zinc, alloys thereof, and similar species which are known to form a highly oxidized surface. The second metallic species may also be applied sequentially through a plurality of plating steps onto the shaped metallic underlayment.

The plating may take place either through an electrolytic process or through employment of an electroless method. Those skilled in the art will appreciate that each of the foregoing plating techniques may be employed intraorally using presently available commercial methods. It will be appreciated that the nature of metallic plating is such that the bond between the plated layer of a second metallic species and the metallic underlayment will be quite strong due to metallic bonding and possibly the formation of a complex metallic alloy layer at the interface of the two metals. It is preferred that the surface of the second metallic layer outward of the underlayment be present in a relatively highly oxidized form to promote bonding with subsequently applied opaqueing materials. Accordingly treatment of the layer with peroxides or otherwise may, optionally be employed to promote such oxidation. It is convenient to plate onto the metallic underlayment an amount of a second metallic species which is sufficient to substantially completely cover the portion of the underlayment thus plated. Substantial quantities of the second metallic species are not presently believed to be beneficial although they may be applied if desired.

The plated surface is contacted with an amount sufficient substantially to obscure the layer of a polymerizable opaqueing agent. Such opaqueing agents may be selected from a wide variety of polymerizable, resin-based materials as are known to those skilled in the art. See in this regard U.S. Pat. No. 3,889,385 and unfilled or sparingly filled versions of U.S. Pat. Nos. 4,491,453, 4,441,625, and U.S. Ser. No. 259,964, now abandoned, all assigned to the assignee of this invention, which disclose a wide variety of resin-based materials which may be so employed. Each of the foregoing patents and applications is included herein by reference to furnish disclosure as to preferred resin-based systems suitable for employment as opaqueing agents in accordance with the present invention. It is preferred that the foregoing materials be filled and/or pigmented so as to improve the opacity thereof. For example, addition of titania, alumina, Schott glass and other opacification agents is preferred. The opaqueing agent is applied in amounts sufficient substantially to obscure the metallic layers to which it is applied. In general, amounts of opaqueing agent sufficient to produce a layer of polymerizable material of from about 0.5 to about 2.0 mm. is sufficient. More may be used, however, such as when sculpting or smoothing to a finished surface is desired.

The foregoing opaqueing agents may be polymerizable through the application of thermal energy, radiation, or actinic light. Of the foregoing, it is preferred that such materials be formulated to be polymerizable through the application of actinic light, especially visible light. Accordingly, sensitizing systems or catalysts suitable for promoting the thermal or photochemical polymerization of the opaqueing agent are preferrably included therein. According to a still more preferred embodiment, a visible light sensitizing agent comprising camphoroquinone and an amine reducing agent are employed to render a polymerizable resin system polymerizable through exposure to visible radiation.

Following the application of the polymerizable opaqueing agent, the same is polymerized through the application of either heat, radiation or actinic light depending upon the chosen formulation for the opaqueing agent. Thus, it is referred that the opaqueing agent be exposed to, for example, visible light and that the opaqueing agent be formulated so as to be sensitive thereto. The foregoing system is especially preferred for intra-oral employment of the present methods as the exposure of living tissue to visible light is considered to be innocuous.

In accordance with another preferred embodiment of the present invention, an adhesion promoting agent is also employed. Thus, the portion of the shaped metallic underlayment which has been plated with a layer of a second metallic species is caused to be more receptive to bonding with the opaqueing agent by application of such adhesion promotion agent. In the alternative, the adhesion promotion agent may be included within the opaqueing agent formulation itself; the two may be applied concurrently.

The adhesion promotion agent generally comprises a di- or polyfunctional material having two types of functionalities. Such materials preferably comprise chemical species having one or more polymerizable functionalities, especially ethylenic unsaturations, together with one or more functionalities capable of either ionically, covalently or coordinately bonding with the surface of the second metallic species. Accordingly, the adhesion promotion agents may be represented by the following general formula:

$$(X)_m - R - (Y)_n \qquad \text{I}$$

wherein R is a hydrocarbyl group having from 1 to about 20 carbon atoms, X is a functionality adapted to bond to the surface of the second metallic species, Y is a polymerizable group and n and m are integers having a value from about 1 to about 3. It is preferred that the polymerizable functionalities, Y, be ethylenic unsaturations which are capable of interpolymerizing with the polymerizable materials of the opaqueing agent. Accordingly, it is preferred that such materials be acrylates, methacrylates and related species. Alternatively, however, such functionalities may be any of the polymerizable functionalities which are disclosed for use in connection with any of the foregoing patent applications which have been incorporated herein by reference. The metallic surface bonding functionalities, X, may be any of a number of functionalities which are capable of relatively strong bonding or association with the surface of the second metallic species.

The bonding functionalities may be selected from ionic species such as phosphates, sulfates and the like which may form inorganic ester bonds with oxide or hydroxylic linkages on the surfaces of the second metallic species. Preferred among this class of promoters is glycerophosphoric acid dimethacrylate, diacrylate, and similar species; pentaerythritol trimethacrylate phosphate, related acrylates; and similar sugar-type acrylics.

In an alternative embodiment, the bonding functionalities may comprise any of a number of silicon-based materials which may form siloxy bonds with the second metallic surface. In general, the bonding of such silicon species with the second metallic species in accordance with the present invention is stronger than similar bonds between silicon species and the surfaces of dental alloys such as gold. For the foregoing reasons, such silicon species may profitably be employed in accordance with the present invention. Among the siliconbased functionalities which may be suitable for employment as bonding substituents on the adhesion promoters of the present invention are any of the wide variety of siloxy species such as trimethoxy, triethoxymethoxy, triethoxy, and many others. Accordingly, adhesion promoters having such silicone functionalities may be represented by illustrative compounds such as γ-methacryloxypropyltrimethoxy-silane.

A third alternative for the adhesion promoters in accordance with the present invention comprises those materials which are capable of coordinating with metallic atoms or ions on the surface of the second metallic species. In this regard, coordination is meant to indicate the formation of bonds of ligature as will be understood by those familiar with the field of inorganic ligand bonding. Among those compositions suitable for use as adhesion promoters in the present invention which employ coordination functionalities to improve the bonding ability with the second metallic surface are vanillic acid, 4-META (4-methacryloxyethoxy mellitic anhydride) and others.

Amounts of adhesion promoter are included in accordance with the present invention which are sufficient to improve the adhesion between the opaqueing agent and the second metallic surface. When the adhesion promoter is applied to the second metallic surface prior to the application of the opaqueing agent, an excess is generally applied and unreacted material removed. When the adhesion promoter is included within the opaqueing agent itself, amounts sufficient substantially to improve the adhesion between the second metallic surface and the opaqueing layer are included therewith. In general, amounts from about 0.001% to about 20% by weight are thus included in the opaqueing agent.

An additional group of adhesion promoters which is suitable for use in connection with the practice of a particular embodiment of this invention is also known. This group comprises the polymerizable acids such as acrylic acid, methacrylic acid, and others which promote adhesion when included as a constituent of the opaqueing agent compositions. The exact mechanism whereby the foregoing acids promote the adhesion of opaqueing agent to metallic surface is not presently understood. It is believed likely that the foregoing involves either ionic or covalent bonds, possibly through the formation of mixed organic-inorganic esters.

FIG. 1 is a partial cutaway view of a crown formed in accordance with the present invention. Thus, the crown 10 is designed to fit upon a dental stump or prosthetic post 12 inserted below the jaw line and preferably in communication with the jaw bone. A metallic underlayment 14 comprising a dental alloy such as a high gold alloy is formed to fit snugly over the post 12 and is adhered thereto. In accordance with FIG. 1, one surface of the underlayment 14 is plated with a layer of a second metallic species 16, here tin. The tin layer 16 is then coated with an opaqueing agent 18 in accordance with the present invention. An amount of opaqueing agent is applied which is sufficient substantially to obsure the layer of tin. An aesthetic veneer 20 has been applied to one surface of the crown 10 so as to present an aesthetically pleasing aspect thereto. The opaqueing layer 18 is well suited to the application of the aesthetic layer 20 through, for example, adhering the two together. In accordance with a preferred embodiment, an adhesion promoter is either interposed between metallic layer 16 and opaqueing layer 18 or included as part of the latter.

Figure 2:
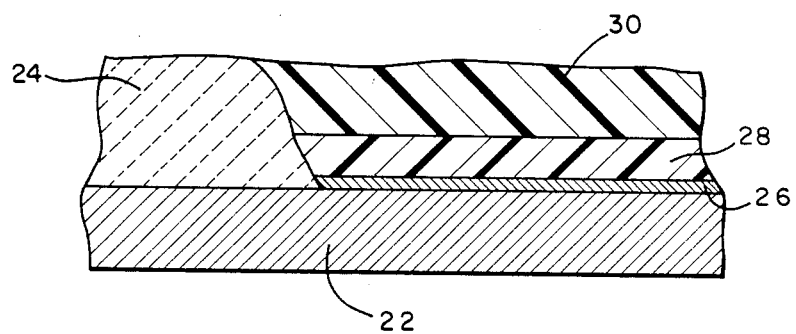
FIG. 2 is a partial cross-sectional view of a repaired dental appliance in accordance with the present invention.

FIG. 2 depicts a cross-sectional portion of a dental appliance repair effected in accordance with the present invention. A metallic underlayment 22 is shown. A continuous layer of porcelain 24 had been in place on the metallic underlayment 22 however a portion thereof has been broken off. Accordingly, the portion of metallic underlayment 22 from which the porcelain has been removed is plated with a layer of a second metallic species 26 such as tin. The tin layer is then obscured through the application of a layer of opaqueing agent 28 in accordance with the present invention. The opaqueing agent is then polymerized to provide a surface for the application of an aesthetic veneer 30 thereto. Through judicious choice of aesthetic veneer 30, a substantially undetectable interface between porcelain 24 and veneer 30 may be presented thus to result in an attractive repair.

EXAMPLE 1

A specimen metal tab ⅜×¾" was cast in accordance with standard technique, using Biobond TM Crown and Bridge Nickel-Chrome Alloy (product of Dentsply International Inc.). The suface of the specimen was prepared by grinding with dental stones and then by paaschéing using an alumina laden air stream with an Air Eraser TM (product of Paasché Airbrush Co.) according to directions. The surface was then brush plated, using Alkaline Tin Plating Solution 5001 (product of Liquid Development Co.) according to directions, involving contacting a remote site of the specimen with a cathode and a metal stylus comprising the anode the end of which is wrapped with a cotton swab for introducing the plating solution onto the metal surface in such a way that the stylus itself does not contact the specimen. The specimen surface was then rinsed first with water, then with dilute hydrogen peroxide, and again with water, and dried using Dust Chaser TM (product of V.W.R. Scientific). (It would be preferred that after paaschéing the surface be cleaned by brushing and rinsing with deionized water).

EXAMPLE 2

Example 1 was modified by applying to the ground surface a dilute hydrochloric-citric acid solution having a pH of 1 while electrifying the specimen with a forward current of 4 amps per square inch at 8 volts in lieu of paaschéing. An adherent layer of tin resulted when the plating procedure of Example 1 was followed.

EXAMPLE 3

The surface of an article of metal can also be plated using the electroless procedure, as follows. Prepare the surface of the article by grinding and paaschéing. The article would be plated by immersion in an electroless tin plating solution, such as Stanomerse TM (product of Gold Rhodium Technic, Inc.) or by brushing on, causing elemental tin to deposit on the surface. Excess solution would be rinsed off with water and/or dilute hydrogen peroxide and then dried.

EXAMPLE 4

A specimen prepared and plated in accordance with Example 1 was primed by applying an adhesion promoter consisting of an 0.3% solution of glycerophosphoric acid dimethacrylate in ethanol, and allowing the ethanol to evaporate.

EXAMPLE 5

An opaquer composition was prepared consisting of:

| Percent by Weight | |
|---|---|
| 8.49% | poly(methyl methacrylate-co-acrylonitrile) (60:40)(molecular weight 350,000 g/mole, avg. size about 50 micron) |
| 8.49 | titanium dioxide |
| 1.87 | Rohm Plex TM 6661-0 |
| 4.66 | methyl methacrylate |
| 0.03 | dimethyl p-toluidine |
| 22.94 | methyl ethyl ketone |
| 53.52 | tetrahydrofuran |
| 100.00% | |

The composition was prepared by milling the polymer, titanium dioxide, methyl ethyl ketone and THF in an Abbé mill for three hours. The remaining ingredients were added and mixed until homogeneous.

Specimens plated in accordance with Example 1 and primed in accordance with Example 4 were selected. An end portion of one surface of each specimen was coated with a layer of the opaquer of this Example, and the solvent was allowed to evaporate. An initiator solution of 1% benzoyl peroxide in diisopropyl ether was applied to the opaqued surface and allowed to dry.

A veneering composition (Biolon TM Crown and Bridge Resin, product of the L. D. Caulk Co.) was applied to the opaqued surface and polymerized according to directions for use of that product at 90° C. and 3 bars pressure for 25 minutes.

EXAMPLE 6

Opaqued and veneered specimens prepared in accordance with Example 5 were stored in deionized water at 50° C. for 94 hours. They were then thermal shock cycled thirty times by immersion first in boiling water for 30 sec., then ice water for thirty seconds. Lap shear specimens were prepared by affixing one end of a ⅜×1" piece of aluminum having a ¼" hole drilled in the other end thereof, to the opaqued and veneered surface of each specimen using Versilok TM 204 structural adhesive (a product of Hughson Chem. Co.). The samples were subjected to a lap shear test by clamping the uncoated surface of a specimen to one set of jaws of an Instron TM test unit, and attaching the free end of the aluminum piece to the other set of jaws using a loop of an orthodontic wire, and then stressing the specimens at 0.5 in/min. to produce a lap shear failure. The specimens of this Example produced a lap shear value of above 395 lbs. per square inch.

EXAMPLE 7

An unpigmented composition was prepared consisting of:

| Percent by weight | |
| --- | --- |
| 4.54% | poly(methyl methacrylate-co-acrylonitrile) (60:40) |
| 4.54 | Rohm Plex TM 6661-0 |
| 0.01 | camphoroquinone |
| 0.05 | methyl diethanolamine |
| 89.04 | dichloromethane |
| 1.82 | amyl acetate |
| 100.00% | |

The ingredients were milled for about one hour until homogeneous. Care was taken to avoid exposing the composition to bright light for any substantial length of time. The composition was applied to an end portion of several specimens of Midas TM Crown and Bridge Type III gold alloy prepared in accordance with Examples 1 and 4, and solvent allowed to evaporate. The coated surface was then exposed to visible light from a Prisma-Lite TM Polymerizaton Unit (product of the L. D. Caulk Co.) for one minute to polymerize the composition. A self-curing acrylic veneering composition (Sevriton TM, product of AD International) was applied to the coated surface and allowed to polymerize in accordance with directions for use of that product. After water storage (88 hours at 50° C.) and thermal shock cycling, and preparation as in Example 6, specimens of this Example resulted in a lap shear value of 810 p.s.i.

EXAMPLE 8

An opaquer composition was prepared from:

| Percent by weight | |
| --- | --- |
| 16.67% | silanated alumina |
| 49.83 | aliphatic urethane acrylate (Uvithane TM 782 of Thiokol) |
| 16.50 | 1,6-hexanediol diacrylate |
| 16.67 | triethylene glycol dimethacrylate |
| 0.08 | camphoroquinone |
| 0.25 | methyl diethanolamine |
| 100.00% | |

The opaquer was applied to specimen alloy tabs of Examples 1 and 4, and after exposure to visible light from a Prisma-Lite TM polymerization unit, a hard cured film was obtained. The opaqued surface is ready for the application of a commercial veneering composition, such as Biodent K&B Plus (product of Zahnfabrik Wienand Sohne & Co., GmbH), and a satisfactory result will be obtained.

EXAMPLE 9

An opaquer composition similar to that of Example 8 was prepared, except using Barium glass filler (product of Schott) in place of alumina, and applied and cured according to Example 8, resulting in a hard cured radiopaque film, ready for application of a commercial veneering composition.

EXAMPLE 10

An opaquer composition was prepared consisting of:

| Percent by weight | |
| --- | --- |
| 10.18% | poly (methyl methacrylate-co-acrylonitrile(60:40) beads about 50 microns in diameter |
| 2.37 | Elvacite TM 2041 polymethyl methacrylate (DuPont) |
| 1.55 | Aerosil TM R972 (DeGussa) |
| 11.78 | Titanium dioxide (No. 328-Whittaker, Clarke & Daniels) |
| 0.78 | A174 silane (Union Carbide) |
| 35.25 | dichloromethane |
| 35.25 | nitromethane |
| 0.16 | acrylic acid |
| 2.68 | trimethylolpropane trimethacrylate |
| 100.00% | |

The dry ingredients, i.e., polymer beads, Elvacite, Aerosil and titanium dioxide, were milled in a ball mill for 45 minutes. The remaining ingredients were added and the mixture ball milled for 45 minutes.

The opaquer was applied to specimens prepared in accordance with Example 1 but the specimens were not primed as in Example 4. Biolon TM resin was applied in accordance with Example 5. Three such specimens were stored in 37° C. water for one week, thermal shock cycled (30 cycles of 30 seconds in boiling water, 30 seconds in ice water) and prepared into lap shear specimens in accordance with Example 6.

These specimens were vacuum dyed with 1% methylene blue solution and tested for lap shear at 0.05 in/min., obtaining an average lap shear value of 699 lb/in$^2$, and resulted in a dye penetration of only 15%.

Five opaqued and veneered specimens were stored in 37° C. water for 4 weeks and lap shear tested without thermal shock cycling, and resulted in an average lap shear value of 510 lb/in$^2$. These specimens exhibited no dye penetration.

Two opaqued and veneered specimens were stored in 37° C. water for 12 weeks and resulted in a lap shear value of 651 lb/in$^2$ without thermal shock cycling. These specimens exhibited no dye penetration and showed excellent stability.

Three opaqued and veneered specimens were stored in 37° C. water for 24 weeks and resulted in a lap shear value of 1140 p.s.i. without thermal shock cycling. They exhibited no dye penetration.

EXAMPLE 11

A lap shear evaluation was conducted on three commercially available crown and bridge repair kits, Denmat TM, Fusion TM and Metalit TM. Each was coated and veneered onto $\frac{3}{8} \times \frac{3}{4}''$ tabs of Biobond TM crown and bridge alloy in accordance with manufacturers' instructions, except that for Fusion, the specimen was completed by coating with Sevriton veneering composition. The specimens were stored in 37° C. water for 210 hours and thermal shock cycled. Each failed at the alloy-opaquer bond during thermal shock.

We claim:

1. A method for the construction of a dental appliance for use in an oral environment comprising:
    (a) providing a shaped underlayment of a first metallic species generally inert with respect to the oral environment;
    (b) plating onto at least a portion of the underlayment a layer of a second metallic species;
    (c) oxidizing a surface portion of said layer to produce an oxide layer overlaying a subsurface layer of said second metallic species, said oxidizing step being capable of performance intraorally;
(d) applying a polymerizable opaqueing agent to said surface portion in an amount sufficient to substantially obscure the oxide layer; and
(e) polymerizing said opaqueing agent, at least one of steps (c), (d) or (e) being performed intraorally.

2. The method of claim 1 further comprising: treating said layer with an adhesion promoter prior to said applying step.

3. The method of claim 2 wherein said promoter has the formula $(X)_m$—R—$(Y)_n$, wherein; R is a hydrocarbyl group having from 1 to about 20 carbon atoms; X is selected from the group consisting of ionic functionalities capable of forming inoganic ester bonds with said second metallic species, silicon species capable of forming siloxy bonds with said second metallic species, or ligand functionalities capable of forming coordination bonds with said second metallic species, Y is an ethylenically polymerizable group, and n and m are integers from 1 to about 3.

4. The method of claim 2 further comprising: applying to the obscured layer a pre-formed dental veneer.

5. The method of claim 1 further comprising: applying to the obscured layer a pre-formed dental veneer.

6. The method of claim 1 further comprising applying a polymerizable veneering composition to said opaqueing agent prior to said polymerizing step.

7. The method of claim 1 wherein said plating comprises electroplating.

8. The method of claim 1 wherein said opaqueing agent comprises a composition polymerizable through exposure to actinic light.

9. The method of claims 1 or 8 wherein said opaqueing agent comprises a blend of a monofuctional monomer and a di- or polyfunctional crosslinking agent for said monomer.

10. The method of claim 1 wherein a polymerization catalyst is applied to the opaqueing layer subsequent to said application step.

11. The method of claim 1 wherein step (b) and all following steps are performed intraorally.

12. The method of claim 1 wherein said construction is a reconstruction.

13. The method of claim 1 wherein said construction is a repair.

14. A method for the construction of a dental appliance for use in an oral environment comprising:
(a) providing a shaped underlayment of a first metallic species generally inert with respect to the oral environment;
(b) plating onto at least a portion of the underlayment a layer of a second metallic species;
(c) oxidizing a surface portion of said layer to produce an oxide layer overlaying a subsurface layer of said second metallic species, said oxidizing step being capable of performance intraorally;
(d) applying to said surface portion a polymerizable agent for adhering; and
(e) polymerizing said agent, at least one of steps (c), (d) or (e) being performed intraorally, and the second metallic species having a greater tendency to bond with the polymerizable adhering agent than does the first metallic species.

15. The method of claim 14 further comprising treating said layer with an adhesion promoter prior to said applying step.

16. The method of claim 15 wherein said promoter has the formula $(X)_m$—R—$(Y)_n$, wherein: R is a hydrocarbyl group having from 1 to about 20 carbon atoms; X is selected from the group consisting of ionic functionalities capable of forming inorganic ester bonds with said second metallic species, silicon species capable of forming siloxy bonds with said second metallic species, or ligand functionalities capable of forming coordination bonds with said second metallic species; Y is an ethylenically polymerizable group; and n and m are integers from 1 to about 3.

17. The method of claim 15 wherein said promoter has the formula $(X)_m$—R—$(Y)_n$, wherein: R is a hydrocarbyl group having from 1 to 20 carbon atoms; X is selected from the group consisting of ionic functionalities capable of forming inorganic ester bonds with said oxidized surface, silicon species capable of forming siloxy bonds with said oxidized surface, or ligand functionalities capable of forming coordination bonds with said oxidized surface; Y is an ethylenically polymerizable group; and n and m are integers from 1 to 3.

18. The method of claim 15 wherein said adhesion promoter is a di- or polyfunctional material having two types of functionalities.

19. The method of claim 14 further comprising applying a polymerizable composition to said agent prior to said polymerizing step.

20. The method of claim 14 further comprising applying to the polymerized adhering agent a performed dental veneer.

21. The method of claim 14 further comprising applying a polymerizable veneering composition to said adhering agent prior to said polymerizing step.

22. The method of claim 14 wherein said plating comprises electroplating.

23. The method of claim 14 wherein a polymerization catalyst is applied to the polymerizable adhering agent subsequent to said application step.

24. The method of claim 14 wherein step (b) and all following steps are performed intraorally.

25. The method of claim 14 wherein said construction is a reconstruction.

26. The method of claim 14 wherein said construction is a repair.

* * * * *